United States Patent [19]
Vilkomerson

[11] Patent Number: 5,425,370
[45] Date of Patent: Jun. 20, 1995

[54] METHOD AND APPARATUS FOR LOCATING VIBRATING DEVICES

[75] Inventor: David Vilkomerson, Princeton, N.J.

[73] Assignee: Echocath, Inc., Monmouth Junction, N.J.

[21] Appl. No.: 216,812

[22] Filed: Mar. 23, 1994

[51] Int. Cl.⁶ ............................................. A61B 8/12
[52] U.S. Cl. ............................................. 128/662.06
[58] Field of Search .............. 128/662.03, 662.04, 128/662.05, 662.06, 660.06, 660.07, 660.02

[56] References Cited

U.S. PATENT DOCUMENTS

| | | | |
|---|---|---|---|
| 4,819,649 | 4/1989 | Rogers et al. | |
| 5,161,536 | 11/1992 | Vilkomerson et al. | 128/662.05 |
| 5,307,816 | 5/1994 | Hashimoto et al. | 128/662.06 |
| 5,329,927 | 7/1994 | Gardineer et al. | 128/662.03 |

Primary Examiner—George Manuel
Attorney, Agent, or Firm—Arthur L. Plevy

[57] ABSTRACT

An ultrasonic imaging system for guiding a user in the placement of an interventional medical device within the body includes a vibrating element which transmits vibratory mechanical oscillation at a predetermined frequency of vibration to the interventional medical device. The medical device oscillates in accordance with the vibratory oscillation so that the interventional medical device completes an oscillation during each vibratory period. An imaging transducer sequentially transmits ultrasonic waves down a selected image line into the imaging region in pulses which are separated by a time interval determined as a function of the vibratory period so that they coincide with maximum displacement of a given point on the interventional device. Return signals received after each pulse are processed to eliminate static and non-static tissue components so that a bright image of the vibrating element is obtained.

22 Claims, 3 Drawing Sheets

METHOD AND APPARATUS FOR LOCATING VIBRATING DEVICES

FIELD OF THE INVENTION

The present invention relates to ultrasonic diagnostic systems which noninvasively image internal parts of the body of a patient under investigation and, in particular, to the use of such systems for guiding the placement of a medical instrument within the body.

BACKGROUND OF THE INVENTION

Ultrasonic diagnostic imaging systems may be used in conjunction with surgical and other invasive procedures to assist in the accurate placement of medical instruments such as needles, trocars, and other medical devices inside the body. For example, U.S. Pat. No. 4,697,595 issued to Breyer et al describes a cardiac catheter and a pacing lead carrying an ultrasonic transducer. When this devices is used in conjunction with an ultrasonic imaging system, the location of the catheter or leads inside the body can be represented in the ultrasonic image by the reception or transmission of ultrasonic signals between the imaging transducer and the transducer mounted on the invasive device. This technique of incorporating ultrasonic transducers into invasive medical instruments has also been applied to needle-type devices, as illustrated in U.S. Pat. No. 3,556,079 issued to Omizo and U.S. Pat. No. 4,249,539 issued to Vilkomerson et al.

In the Omizo patent, Doppler interrogating waves are directed forward from the tip of a biopsy needle. As the needle penetrates the body, backscatter waves from moving fluids within a vessel or organ are received and a conventional Doppler beat frequency is detected. The reception of the Doppler tone provides an indication that the needle is aimed at the vessel or organ containing the fluid; if the needle becomes misdirected, no backscatter waves are returned and the Doppler tone ceases.

Recognizing the inherent limitations of the highly directional Omizo technique, the '539 patent discloses a system with an omnidirectional transducer located at the needle tip. When used in conjunction with an imaging transducer, the omnidirectional transducer is able to exchange ultrasonic waves with the imaging transducer irrespective of its orientation with the imaging transducer, thereby enabling the '539 system to continually provide a visual marker in the ultrasonic image which indicates the needle tip location. However, the '539 system places several critical demands on its user, such as a physician performing a biopsy procedure. An ultrasonic imaging transducer scans over a relatively planar portion of the body, which is depicted in a two-dimensional image. The needle, however, is free to move in three dimensions as it penetrates the body. Hence, the '539 system operates well for its intended purpose when the needle tip is located within the scan plane, but its operation can be ambiguous when the physician first penetrates the body and attempts to achieve that orientation. Under these initial conditions of the procedure the physician must focus his attention on the insertion and guidance of the biopsy needle as it penetrates the patient's body. At the same time the physician must manipulate the imaging transducer and watch the imaging monitor to simultaneously orient the transducer and needle so that both the tissue structure which is to be biopsied and the needle tip are in the image plane. The simultaneity of both the biopsy procedure and the imaging procedure impose considerable demands on even highly skilled practitioners.

To varying degrees the systems and techniques disclosed in the above described patents enable the tip of an interventional device such as a needle to be sharply visualized in the ultrasonic image by reason of the presence of the active transducer element in association with the needle, and particularly when it is located at the needle tip. These techniques have two significant drawbacks, however. One is the construction of a highly miniamrized transducer for in vivo use, and the accompanying concerns for patient safety. The second is the need for significant system integration required to synchronize signals to and from the biopsy needle transducer with the signals of the imaging scanhead. While potentially offering the advantages of high needle visibility and precision, therefore, these active and invasive techniques pose significant implementation dilemmas.

The principles of a technique for passively visualizing a biopsy needle in a color ultrasound imaging system was reported in the Journal of Ultrasound in Medicine, Vol. 9, at pp 243–45 (1990). There it was noted that the passage of biopsy needles or their guide wires was distinctly evident on color Doppler images as the needle or guide wire was being moved. Hand manipulation of a biopsy needle or guide wire, it was found, provided a color image that corresponded to the shaft of the needle. Such a technique is inherent in the physical principles of Doppler imaging, and is in many cases preferable to the above active techniques by reason of its simplicity and lack of need for additional system integration. The technique suffers shortcomings in that the image of the needle is only highly defined when the needle is being manipulated, and is a coarse representation of the entire needle shaft. Recognizing the aforementioned shortcomings, U.S. Pat. No. 5,095,910, entitled ULTRASONIC IMAGING OF BIOPSY NEEDLE and issued to Powers on Mar. 17, 1992 describes a system for imaging an interventional device with ultrasound. In the '910 patent, the tip of a biopsy needle is reciprocated to produce a highly directional motion, thereby causing a Doppler response detectable by a color ultrasonic imaging system. The '910 patent describes reciprocation of a biopsy needle over a wide range of frequencies whereby the reciprocation of the needle tip results in a Doppler shift which is detected via Doppler signal interrogation.

In a copending application Ser. No. 08/022,112 filed on Feb. 25, 1993 and entitled APPARATUS AND METHOD FOR LOCATING AN INTERVENTIONAL MEDICAL DEVICE WITH AN ULTRA SOUND COLOR IMAGING SYSTEM, one of the applicants for the present invention describe a system in which the tip of a needle or other interventional device is visualized in vivo using a color ultrasonic imaging system. Disclosed therein is an apparatus and method for causing a periodic or oscillating mechanical motion in the interventional medical device which results in a significant Doppler shift effect that enables the device to be detected by the color ultrasonic imaging system.

As indicated above, both the '910 system and the system disclosed in U.S. patent application Ser. No. 08/022,112 rely upon the use of a moving needle and a color imaging system to detect the Doppler response produced thereby. While each of these systems avoids the use of invasive transducers and permits the tip of the biopsy needle or other interventional device to be continuously visualized, there are certain drawbacks associated therewith. First, insofar as color imaging systems are designed to be sensitive to the relatively small motion (measurable in microns) of blood in arteries, strong echoes are suppressed and weak echoes enhanced (this is because blood produces weak echoes and tissue artifacts produce strong echoes). Since needles and other metallic interventional devices also produce strong echoes, the device echoes produced thereby are likewise suppressed. Further, the availability to the typical practitioner of the color ultrasound imaging systems contemplated by the '910 patent and the aforementioned application is frequently limited by the large capital investment required for color ultrasound.

It is therefore an object of the present invention to provide an ultrasonic imaging system which does not require the capital investment associated with sophisticated color ultrasonic imaging systems but which still enables the practitioner to continually visualize the needle without the need for the invasive transducers associated with conventional techniques.

SUMMARY OF THE INVENTION

The present invention is directed to a method and apparatus for causing a periodic or oscillating mechanical motion in an interventional medical device such as a biopsy needle to be made visible on inexpensive ultrasound equipment. The known frequency of oscillation is utilized to time the pulses supplied to the imaging transducer so that a given point on the medical device has moved a maximum distance between pulses. In accordance with the principles of the present invention, the oscillating medical device is visualized within the body through ultrasonic imaging.

An ultrasonic imaging system constructed in accordance with the present invention comprises vibrator means operative to transmit vibratory mechanical oscillation at a predetermined frequency of vibration to the interventional medical device in the form of flexural waves and to cause the medical device to oscillate in accordance with the flexural waves. The interventional medical device completes one oscillation during a vibratory period. For selected lines of an image displayed by the imaging system, the imaging transducer directs a sequence of at least two send or imaging pulses in the form of ultrasonic waves along substantially the same line to the region of the body in which the medical device is being manipulated. The sequence of the send pulses is such that they are separated in time by an interval which is a function of said vibratory period.

Preferably, the send pulses are separated in time by an odd number of one-half multiples of the vibratory period of the medical device. The driving means may be adapted to supply at least two send pulses for each line of an image displayed by the ultrasonic imaging system, but may be configured to supply the pulses for every nth line, where n is a positive integer, if desired.

The system includes processing means in which is stored reflected pulse signals corresponding to the imaging pulses sent during each sequence and which is adapted to compensate for static and non-static tissue signal components in the reflected pulse signal received after each send pulse.

A method of utilizing the imaging system of the present invention for placement of an interventional medical device within an interior region of a body comprises the steps of ultrasonically imaging the interior region with an ultrasonic imaging system which produces a structural image of the interior region, inserting an interventional medical device into the imaged region, and vibrating the medical device at a predetermined frequency to create flexural waves in the medical device. The interventional medical device completes one vibratory oscillation during each vibratory period. Pulses separated in time by an interval determined as a function of the vibratory period are supplied to an imaging transducer of the system.

Corresponding return echo signals following each respective pulse are stored and utilized to compensate for static and non-static tissue signal components in the return echo signals. A visual signal is developed from the return echo signals for locational display of the medical device with respect to the ultrasonically imaged region. Reliable measurement of the displacement is assured by, in the next frame, shifting the relative phase of the sound pulses with respect to the vibratory drive by 90°. If the depth of the image permits, four imaging pulses are supplied for each vibratory period, a set of first and second pulses being provided to be equivalent to first and second frames of the image.

DETAILED DESCRIPTION OF THE INVENTION

Figure 1:
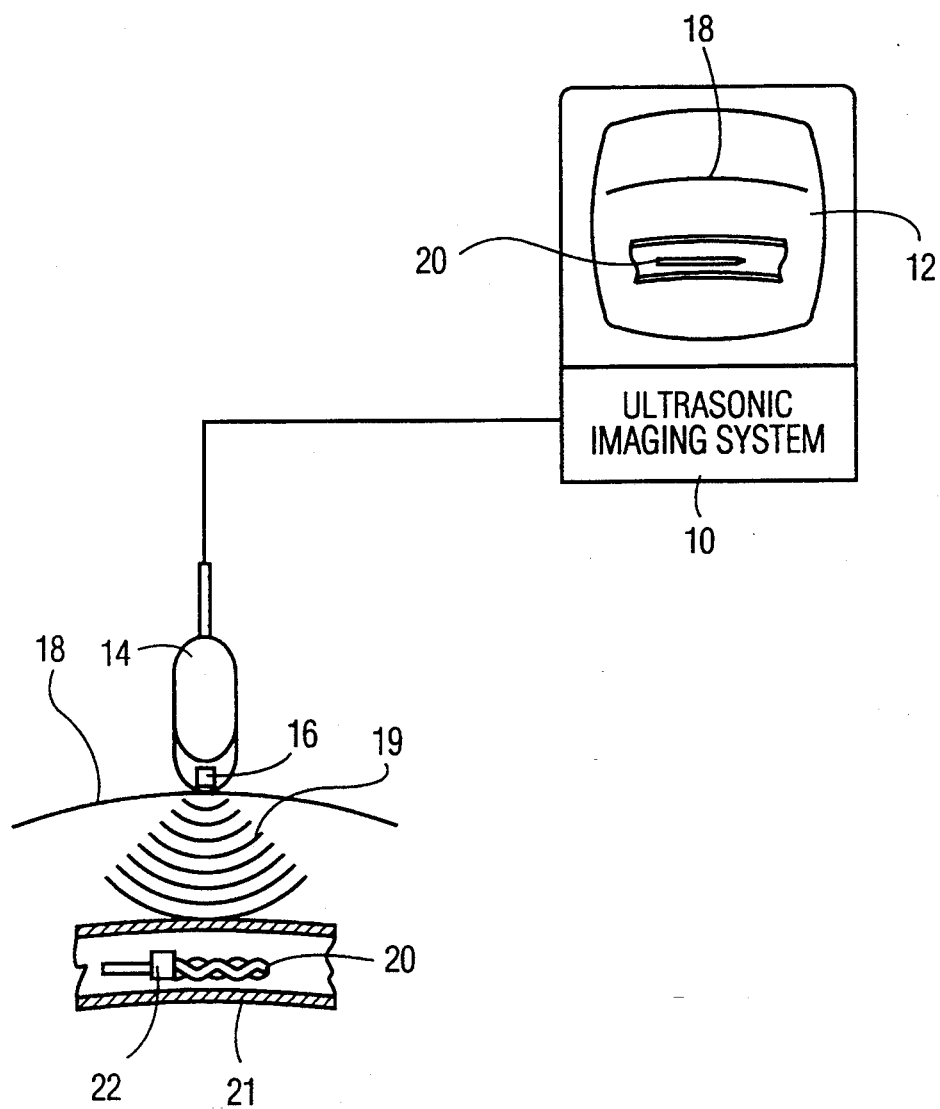
FIG. 1 is a block diagram showing an ultrasonic imaging system for visualizing a vibrating interventional medical device in accordance with the present invention.

Referring to FIG. 1, there is shown a simple block diagram of an illustrative ultrasonic imaging system employing the present invention. The ultrasonic imaging system 10 includes a display 12, which enables the practitioner or user of the system to visualize the portion of the patient's body that is being scanned. Ultrasonic system 10 further includes a scanning head 14 having an imaging transducer 16 in contact with the surface 18 of the skin of a patient. In the illustrated embodiment, the scanning head 14 is a hand-held unit which the practitioner manually moves about the body of a patient to thereby perform imaging according to a particular ailment or complaint.

As shown in FIG. 1, the scanning head 14 provides a beam of ultrasonic waves 19 into the body of a typical patient under investigation. As indicated, it is desired to utilize ultrasound to trace the progress of a biopsy needle or other interventional medical device which may be inserted into a breast, artery, vein, or other body part of the patient. As seen in the FIG. 1, a needle 20 is inserted into an artery 21 of a patient and is oscillated by a mechanical means 22 such as that described in U.S. patent application Ser. No. 08/022,112. The disclosure of the aforementioned patent application is expressly incorporated herein by reference. In accordance with the present invention, the display 12 depicts the artery as well as the needle so that the physician in viewing the display is able to determine the progress of the needle. Such a display is made possible by the novel manner in which the echo signals are processed by the apparatus of the present invention.

As will be appreciated by those of ordinary skill in the art, in a conventional ultrasound system each pulse produces a line of the image, the image consisting of brightness pixels proportional to the received reflected energy. The present invention advantageously utilizes the frequency of vibration of the interventional device, which is known, to enhance visualization of the vibrating device by a sequence of pulses along the same or substantially similar line. The timing of these pulses is determined by the vibratory frequency of the device.

Figure 2:
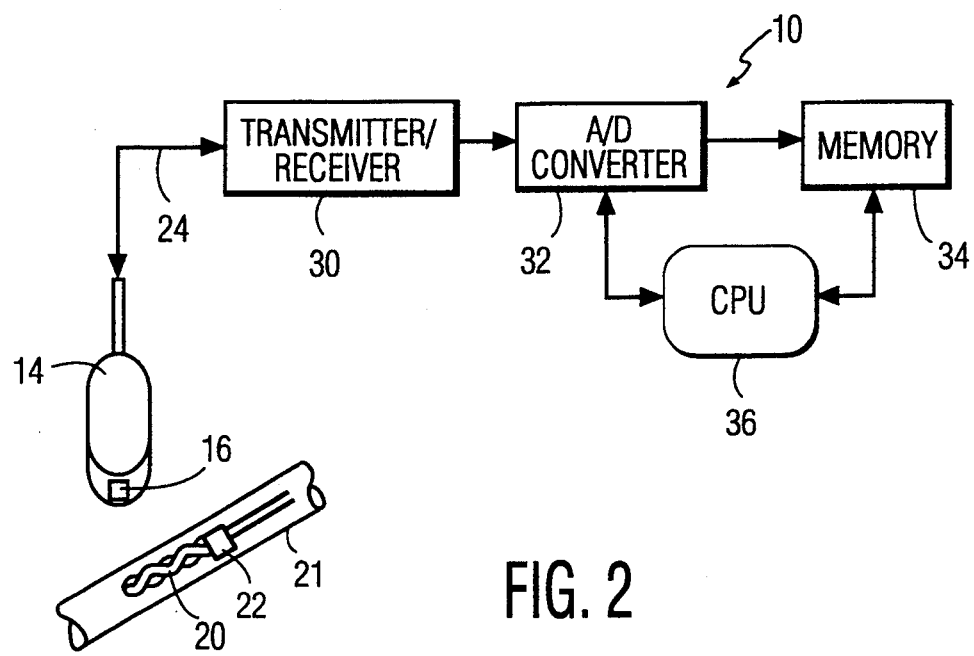
FIG. 2 is a detailed block diagram showing the components of an ultrasonic imaging system constructed in accordance with the present invention.

With reference now to FIG. 2, it can be seen that the scanning head 14 is connected by a cable 24 to a receiver module 30, which module includes a transmitter unit for supplying energizing pulses or waves to the transducer 16. In a conventional manner, the scan head 14 operates to transmit the pulses supplied by the transmitter unit during a transmit mode and to receive corresponding reflected pulses during a receive mode. The scan head 14 thus serves the dual purpose of transmitting a pulse and receiving a reflected or echo pulse after transmission, within a predetermined time interval. While usual non-color systems transmit one imaging pulse per image line, in the present invention several pulses along some or all of the lines is employed.

An analog to digital converter 32 receives the echo pulses from the transducer, converts them into digital echo pulse signals, and stores the digitized signals in a memory 34. When a predetermined sequence of digital echo pulse signals has been stored, one is subtracted from another by CPU 36 to obtain a difference signal. Since each echo pulse signal is essentially from the same tissue along the line, the major difference in the echo pulse signals is the position of the vibrating device 20. The difference signal is thus indicative of a change in position along a scan line. (This is well-known in radar as moving target indicator (MTI) which is known to be used in ultrasound systems.)

In accordance with one embodiment of the present invention, two pulses are sent for each line of the image, the pulses preferably being separated in time so that the vibrating device has oscillated the greatest distance (i.e. at one half of the vibratory period $P_v$). Using conventional ultrasound equipment, for example the round trip for each pulse is 133 microseconds ($\mu s$) at an image depth of ten centimeters. Accordingly, so long as $P_v$ is greater than 266 $\mu s$ (i.e. a vibratory frequency of 3.75 KHz or less), the aforementioned $P_v/2$ pulse sequence may be used. It will of course be readily understood that for greater depths or higher vibrational frequencies, a pulse interval of 1½ vibratory periods, or any odd number of half periods, can be used to ensure that the pulse coincide with the maximum motion of the interventional device.

Figure 3A:
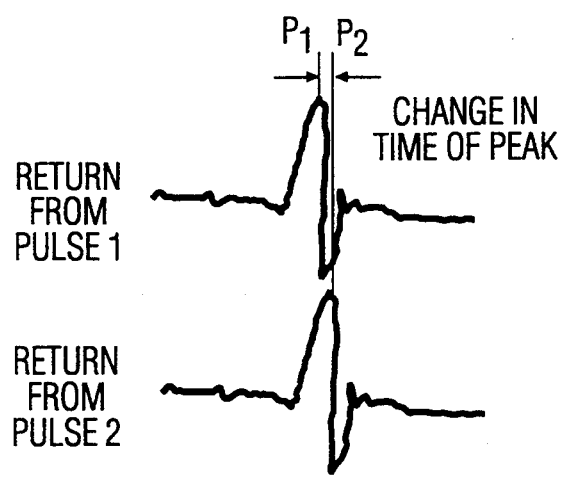
FIG. 3A is a graphical representation of first and second return signals obtained after directing first and second pulses into the region of the body under investigation.
Figure 3B:
FIG. 3B is a graphical representation of a difference signal obtained in accordance with one technique of utilizing the present invention.

As shown in FIG. 3A, a first echo signal $s_1$ is received by receiver 30 after pulse $P_1$ is transmitted. In a similar fashion, a second echo signal $s_2$ is received by the receiver 30 after pulse $P_2$ is transmitted. CPU 36 receives the digitized echo signals and forms a difference signal $s_\Delta$ such as the one shown in FIG. 3B. The amplitude of the difference signal $s_\Delta$ resulting from the subtraction is approximated by the following formula:

$$A_\Delta = 4\pi X_s A_n / \lambda$$

where:
$A_\Delta$ is the amplitude of the difference signal;
$X_s$ is the displacement of the interventional device;
$\lambda$ is the wavelength of the ultrasonic frequency used; and
$A_n$ is the amplitude of the needle echo The signal size as a function of displacement is determined as follows. To calculate the signal obtained from vibrating the device and subtracting the signal from the second pulse from the first, assume that the ultrasound reflected signal from the device is (at this point assuming an arbitrary phase of 0)

$$O_1 = A \sin(\omega t)$$

and if the device moves a distance $\Delta d$, the phase of the reflected wave is changed because the time of the reflection from the device is increased by twice the distance divided by the speed of sound in the medium, so the backscattered signal is now $$O_2 = A \sin(\omega(t + 2\Delta d/v)).$$

The sine can be expanded, and if $\omega \Delta d/v$ is small, then the cosine part of the expansion equals 1 and we have $$O_2 = A \sin(\omega t) + A \sin(2\omega \Delta d/v) \cos \omega t$$

So using $$107\ \Delta d/v \rightarrow 2\pi f \Delta d/f\lambda,$$

then $$O_2 - O_1 = (4\pi \Delta d/\lambda) A \cos \omega t.$$

If we choose $\omega t$ to be $n\pi$, then we have the maximum difference in signal of 4 pi times the displacement of the device divided by the wavelength of the ultrasound being used, multiplied by the amplitude of the device echo.

It will be readily appreciated that any echoes corresponding to non-moving tissue will cancel out, while those of the vibrating device will not. It should also be apparent that the reason for timing the pulses to coincide with maximum displacement of the vibrating device is that it results in the largest difference signal. It is, however, contemplated that other pulse sequences may be employed subject to the limitations attributable to image depth and device vibrational frequency, as discussed above.

Displacements typically obtained by vibrating an interventional device such as a needle are on the order of 10 microns, which is 0.03 of a 5 MHz wavelength (a wavelength commonly used for diagnostic ultrasound). Accordingly, the difference signal obtained is about ⅓ of the needle reflection signal. As the needle is itself a much better reflector than tissue, the differenced needle signal $s_\Delta$ is much bigger than the differenced tissue signal.

The difference signal $s_\Delta$, after proper scaling, corresponds to a brightness image of the vibrating elements. In order to display the position of the vibrating elements within the body of the patient as illustrated in FIG. 1, the brightness image is overlaid in a conventional manner on the standard B-scan image.

Figure 4:
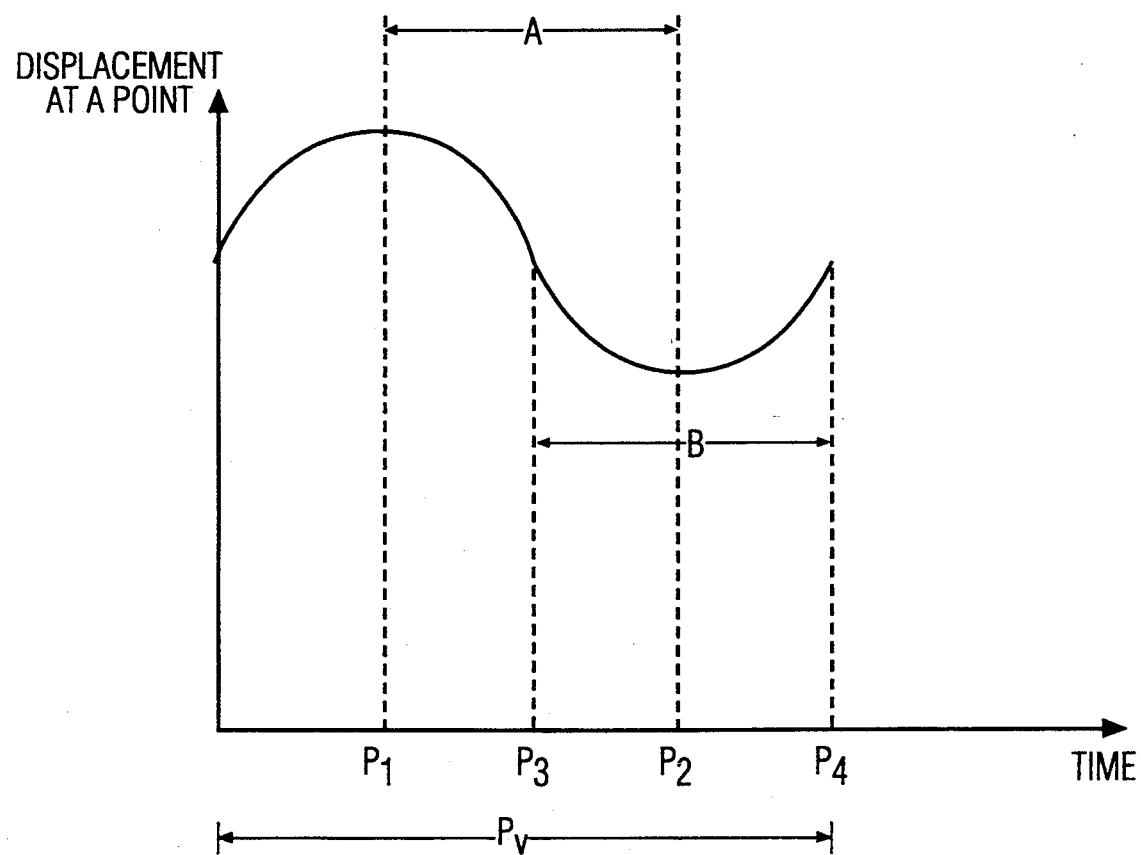
FIG. 4 is a graphical representation showing displacement of a given point on the interventional device as a function of time to illustrate the desirability of modifying the pulse times in accordance with a modified technique utilizing the present invention.

FIG. 4 illustrates possible pulse sequences which may be obtained during operation of the apparatus in the manner discussed above. As will be apparent from FIG. 4, at a given point on the device, maximum displacement in one direction coincides with pulse $P_1$ while maximum displacement of the device in the opposite direction coincides with pulse $P_2$. Thus, the sequence of $P_1$ and $P_2$ results in the largest difference signal, and hence, the brightest device image. However, at the same point on the device, a different sequence of pulses $P_3$ and $P_4$, separated by the same interval of time as $P_1$ and $P_2$, results in a displacement difference of zero.

In accordance with the present invention, the disappearance of apparent motion caused by the particular choice of pulsing time can be eliminated by advancing or retarding the relative time position of the pulses referenced to the vibratory frequency. Frame-to-frame "quadrature detection" is accomplished as follows.

To calculate the difference signal amplitude hereinabove when determining signal size as a function of displacement we assumed a zero arbitrary phase shift between the device motion and the sampling signals of $O_1$ and $O_2$. As we apply the vibration to the device at one end and the actual phase between the driving sinusoid and the motion of the device depends upon where in time and space the sampling pulses strike the device, we have an unknowable phase shift $\phi$. Therefore, if we call the amplitude of the difference signal found hereinabove "d", we have as a signal for the first pair of sampling pulses $$S1 = d \cos(\omega t + \phi)$$

which of course can be anything from d to 0 in amplitude, depending upon $\phi$. The next time that particular point on the device is struck with an ultrasound pulse would be the next frame. If during this frame the sampling pulses were offset in time, in relation to the driving sinusoid of the device by $\pi/4$, i.e. 90°, (or any odd integer times $\pi/4$) the signal size vs. displacement equations hereinabove would be changed to give $$S2 = +d \sin(\omega t + \phi)$$

and by taking the two signals, squaring and summing them, we obtain $$S = d^2(\sin^2(\omega t + \phi) + \cos^2(\omega t + \phi))$$
$$= d^2.$$

We can obtain this elimination of the arbitrary phase of the device by this means in other ways: we can, if the pulse repetition rate of the ultrasound system can be fast enough (which depends upon the depth to be interrogated), send 4 pulses out for any particular line, breaking them into two pairs of pulses at 180° between each pair and at 90° to each other to obtain this result. Alternatively, we can combine quadrature-staggered pulse pairs from two adjacent lines when the distance along the device is short compared to the spatial wavelength, i.e. when the change in phase due to being at a different point on the device is small enough to allow the above operation to be approximately correct.

In addition, brightening the position of the device after every two frames produces a blinking effect that is helpful for easy visualization of the signal.

As indicated above, the present invention utilizes a difference signal in which the echoes of stationary tissue cancel each other out. However, while this cancellation may occur when the tissue surrounding the vibrating device is static, as a result of respiration, heart beating, and other involuntary movements the tissue or organs under investigation may indeed move. The effects of such movements may be suppressed by using a three pulse sequence along each ultrasound line. The first pulse provides the reference set of values along that line. The second pulse, which is sent half the vibratory period later, is subtracted from the data stored from the reference pulse so that all static reflections will cancel out to leave the vibrating element reflections in a first difference signal. A third pulse is sent at another half-vibratory period interval, and the difference between the second and third pulse is subtracted from the first difference signal. As the difference between the second and third pulse is opposite to the difference between the first and second pulse, subtracting the difference signal adds strength to the needle echo. However, because movement of the tissue is slow, it continues to move in the same direction (unlike the vibrating element echoes) so that when the second difference signal is subtracted from the first difference signal, the "moving" tissue echo components of each cancel each other out. Thus, it can be seen that by using three pulses and processing the difference signals in a manner such as described above, both static and moving tissue signal components may be removed while the signal for the vibrating element is, in fact, increased.

Where three pulses are utilized, the quadrature sampling technique discussed earlier may be employed without modification. Specifically, alternate flames would have the first-pulse time change its phase relative to the vibratory frequency by one quarter of a vibratory period.

If increased signal noise results from random tissue motion or low device reflectivity, the above described three-pulse method can be modified to utilize any number of pulses (4, 5, 6, etc.) When modified in such a manner, it has been found that the needle echo amplitude increases in direct proportion to the number of pulses while the amplitude of the tissue echoes, in the worst case, increases in direct proportion to the square root of the number of pulses.

It should be readily appreciated by those of ordinary skill in the an that it is not necessary that every image line be used for motion detection. Thus, despite the multiple pulses needed per line, the overall frame time need not be increased by the number of pulses used. For example, if three pulses are used on every line, the frame time increases by a factor of three. However, if every fifth scan line is used for motion detection, a "dotted line" image of the interventional device is produced in which there will be 7 pulses for 5 lines (4 regular one-pulse lines and 1 three-pulse line).

While the foregoing has described one embodiment of an ultrasonic imaging system and method for guiding the placement of a medical instrument within the body of a patient under investigation, it is envisioned that further equivalent configurations, modifications, and alternate embodiments may be suggested to those knowledgeable in the art. Accordingly, such alternate embodiments are to be construed as being within the spirit of the present invention even though not explicitly set forth herein, the present invention being limited only by the content and scope of the claims appended hereto.

What is claimed is:

1. An ultrasonic imaging system including an ultrasonic imaging transducer which transmits send pulses and receives reflected pulses corresponding thereto for use in locating an interventional medical device within an interior region of a body under investigation, comprising:

vibrator means operative to transmit vibratory mechanical oscillation at a predetermined frequency of vibration to said interventional medical device and to cause said medical device to oscillate in accordance therewith, said interventional medical device completing one oscillation during a vibratory period;

means for supplying a sequence of said send pulses separated in time by an interval determined as a function of said vibratory period to said imaging transducer; and processing means responsive to said reflected pulses for providing a signal indicative of the position of said medical device, wherein said processing means receives and stores a corresponding reflected pulse signal for each send pulse and compensates for static tissue signal components in said reflected pulses.

2. The system according to claim 1, further comprising means for selecting a line of an image displayed by said ultrasonic imaging system;

wherein each said sequence supplying means is adapted to supply at least two send pulses on each selected line of said image displayed by said ultrasonic imaging system.

3. The system according to claim 2, wherein said send pulses are separated in time by one-half the vibratory period of said medical device.

4. The system according to claim 2, wherein said send pulses are separated in time by an odd number of one-half multiples of said vibratory period.

5. The system according to claim 2, wherein said sequence supplying means is adapted to supply at least two send pulses for each line of an image displayed by said ultrasonic imaging system.

6. The system according to claim 2, wherein said sequence supplying means is adapted to supply at least two send pulses for every predetermined number of lines of an image displayed by said ultrasonic imaging system.

7. The system according to claim 1, wherein said processing means produces a difference signal by subtracting said reflected pulse signals, wherein signal components correspond to static tissue are substantially eliminated.

8. The system according to claim 1, wherein said sequence supplying means is adapted to supply number of pulses to said imaging transducer for selected lines of an image displayed by said system, said processing means being adapted to compensate for non-static tissue signal components in said reflected pulse signals.

9. The system according to claim 8, wherein said processing means obtains a first difference signal by subtracting a second reflected pulse signal from a first reflected pulse signal, produces a second difference signal between said second reflected pulse signal and a third reflected pulse signal, and produces a third difference signal by subtracting said first and second difference signals, wherein signal components corresponding to static and non-static tissue in said body are substantially eliminated.

10. A method for imaging placement of an interventional medical device within an interior region of a body comprising the steps of:

ultrasonically imaging said interior region with an ultrasonic imaging system which produces a structural image of said interior region;

inserting an interventional medical device into the imaged region;

vibrating said medical device at a predetermined frequency, said interventional medical device completing one vibratory oscillation during a vibratory period; and processing reflected pulse signals corresponding to said send pulses, wherein said processing includes compensating for static tissue signal components in said reflected pulse signals and developing a visual signal from said return echo signals for locational display of said medical device with respect to the ultrasonically imaged region.

11. The method according to claim 10, further comprising the steps of:

selecting a line of an image displayed by said ultrasonic imaging system; and directing at least two send pulses into said interior region for each line selected.

12. The method according to claim 11, wherein at least two send pulses are directed into said interior region for each line of an image displayed by said ultrasonic imaging system.

13. The method according to claim 11, wherein at least two send pulses are supplied for every predetermined number of lines of an image displayed by said ultrasonic imaging system.

14. The method according to claim 10, wherein said send pulses of said sequence are separated in time by one-half of said vibratory period.

15. The method according to claim 10, wherein said send pulses of said sequence are separated in time by an odd number of one-half multiples of said vibratory period.

16. The method according to claim 10, further including storing a reflected pulse signal corresponding to each send pulse of a sequence prior to said processing step.

17. The method of claim 10, wherein a difference signal is obtained during said processing step by subtracting a first of said reflected pulse signals from a second of said reflected pulse signals, wherein reflected pulse signal components correspond to static tissue are substantially eliminated.

18. The method according to claim 10, wherein a number of pulses are supplied for selected lines of an image displayed by said system, and wherein said processing step includes the step of compensating for static and non-static tissue signal components in said return echo signals.

19. The method according to claim 10, a first difference signal is obtained during said processing step by subtracting a second reflected pulse signal from a first reflected pulse signal, a second difference signal is obtained by subtracting said second reflected pulse signal from a third reflected pulse signal, and a third difference signal is obtained by subtracting said first and second difference signals, wherein signal components corresponding to static and non-static tissue in said body are substantially eliminated.

20. The method according to claim 10 wherein four or more send pulses are directed into said interior region during each vibratory period for a selected scan line.

21. The method according to claim 20, wherein a set of first and second send pulses are provided for first and second frames of an image displayed by said system.

22. The method according to claim 21, wherein in said second frame, a first send pulse is supplied at one quarter of the vibratory period changed in relation to a first send pulse supplied in said second frame.

* * * * *